United States Patent
Saini et al.

(10) Patent No.: US 10,845,313 B2
(45) Date of Patent: *Nov. 24, 2020

(54) METHODS AND APPARATUS FOR DETERMINATION OF HALOHYDROCARBONS

(71) Applicant: AMS Trace Metals, Inc., Sunnyvale, CA (US)

(72) Inventors: Harmesh K. Saini, Santa Clara, CA (US); Michael J. West, San Jose, CA (US); Qin Wang, San Jose, CA (US); James Garvey, San Jose, CA (US); Paul Rand, San Jose, CA (US); Mark Angelo, San Jose, CA (US); David Johnston, San Jose, CA (US); Robert Ormond, San Jose, CA (US); Ye Han, San Jose, CA (US)

(73) Assignee: AMS Trace Metals, Inc., Wilmington, DE (US)

(*) Notice: Subject to any disclaimer, the term of this patent is extended or adjusted under 35 U.S.C. 154(b) by 195 days.

This patent is subject to a terminal disclaimer.

(21) Appl. No.: 16/004,189

(22) Filed: Jun. 8, 2018

(65) Prior Publication Data
US 2019/0079020 A1 Mar. 14, 2019

Related U.S. Application Data

(63) Continuation of application No. 14/819,454, filed on Aug. 6, 2015, now Pat. No. 10,018,567, which is a
(Continued)

(51) Int. Cl.
*G01N 21/78* (2006.01)
*G01N 33/18* (2006.01)
*G01N 21/75* (2006.01)

(52) U.S. Cl.
CPC ......... *G01N 21/78* (2013.01); *G01N 33/1826* (2013.01); *G01N 21/75* (2013.01);
(Continued)

(58) Field of Classification Search
CPC ........ G01N 21/78; G01N 21/77; G01N 21/75; G01N 33/1826; G01N 33/18
(Continued)

(56) References Cited

U.S. PATENT DOCUMENTS 5,358,875 A  10/1994 Goswami
5,547,877 A   8/1996 Friedman
(Continued)

FOREIGN PATENT DOCUMENTS

CN  101952704 A  1/2011
JP  2008145163 A  6/2008
(Continued)

OTHER PUBLICATIONS

Pack, Brian, et al, Determination of Halogenated Hydrocarbons by Helium Microwave Plasma Torch Time-of-Flight Mass Spectrometry Coupled to Gas Chromatography, Anal. Chem. 1998, 70, 3957-3963. (Year: 1998).*

(Continued)

*Primary Examiner* — Christine T Mui
(74) *Attorney, Agent, or Firm* — Marc P. Schuyler (57) ABSTRACT

A real-time, on-line method and analytical system for determining halohydrocarbons in water which operate by (1) extracting on-line samples; (2) purging volatile halohydrocarbons from the water (e.g., with air or nitrogen); (3) carrying the purge gas containing the analytes of interest over a porous surface where the analytes are adsorbed; (4) recovering the analytes from the porous surface with heat (thermal desorption) or solvent (solvent elution) to drive the analytes into an organic chemical mixture; (5) generating an
(Continued)

optical change (e.g., color change) in dependence upon a reaction involving the analytes and a pyridine derivative; and (6) measuring optical characteristics associated with the reaction to quantify the volatile halogenated hydrocarbon concentration.

22 Claims, 6 Drawing Sheets

Related U.S. Application Data continuation of application No. 13/640,312, filed as application No. PCT/US2011/032438 on Apr. 14, 2011, now Pat. No. 9,134,290.

(60) Provisional application No. 61/326,717, filed on Apr. 22, 2010.

(52) U.S. Cl.
CPC ............ *G01N 33/18* (2013.01); *Y10T 436/19* (2015.01); *Y10T 436/193333* (2015.01)

(58) Field of Classification Search
USPC ........................................................ 436/125
See application file for complete search history.

(56) References Cited

U.S. PATENT DOCUMENTS

| | | | |
|---|---|---|---|
| 8,616,051 B2 | 12/2013 | Kimour | |
| 9,134,290 B2 * | 9/2015 | Saini ................. | G01N 33/1826 |
| 9,222,921 B2 | 12/2015 | Saini et al. | |
| 9,903,844 B2 | 2/2018 | Saini et al. | |
| 10,018,567 B2 * | 7/2018 | Saini ................. | G01N 33/1826 |
| 2003/0092196 A1 | 5/2003 | Saini et al. | |
| 2006/0210440 A1 | 9/2006 | Potyrailo et al. | |
| 2010/0204924 A1 | 8/2010 | Wolfe et al. | |
| 2015/0293070 A1 | 10/2015 | Emmert | |

FOREIGN PATENT DOCUMENTS

| | | |
|---|---|---|
| JP | 2008241606 A | 10/2008 |
| JP | 2009014382 A | 1/2009 |
| WO | 2011133383 A | 10/2011 |
| WO | 2012158388 A | 11/2012 |
| WO | 2017155896 A | 9/2017 |

OTHER PUBLICATIONS

Kaiser, Klaus et al, Determination of Volatile Halogenated Hydrocarbons in Water by Gas Chromatography, Analytical Chemistry, Dec. 1976, vol. 48, No. 14, pp. 2207-2209. (Year: 1976).*
Wang et al., "continuous on-line monitoring of haloacetic acids via membrane extraction," Journal of Chromatography A, 1089 (2005) 39-44.
EP Search Report for EP application 11772452-6, dated Aug. 12, 2014, 6 pages.
PCT/US2011/032438, ISR-WO, 10 pages, dated Dec. 20, 2011 (ISR-WO for international stage of parent, U.S. Pat. No. 9,134,290).
"Seasonal variations of trihalomethanes (THMs) in water distribution networks of Istanbul City," Desalination 176 (2005) 127-141, 0011-9164/05, 15 pages.
"Investigation of bromide ion effects on disinfection by-products formation and speciation in an Istanbul water supply," Uyak et al., Journal of Hazardous Materials 149 (2007) 445-451, 7 pages, Apr. 7, 2007.
"Seasonal variations of disinfection by-product precursors profile and their removal through surface water treatment plants," Uyak et al., Scients of the Total Environment, 390 (2008) 417-424, Nov. 13, 2007, 8 pages.
"THMs assessment in Khuzestan rural water treatment plants," Ahmadi et al., International Journal of Environmental Health Engineering, V1:6, Jun. 2012, pp. 39-43.
"Field and material-specific simulated distribution system testing as aids to understanding trihalomethane formation in distribution systems," Brereton et al., Can. J. Civ. Eng. 29: 17-26 (2002), pp. 17-27.
"Modeling trihalomethane formation for Jabal Amman water supply in Jordan," Al-Omari et al., Environmental Modeling and Assessment 9: 245-252, 2004.
Wang et al., "Microfluidic supported liquid membrane extraction," May 10, 2005, Analytica Chimica Acta 2005 92-98.
Carrero et al., "Analysis of haloacetic acid mixtures by HPLC using an electrochemical detector coated with a surfactantnafion film," Talanta 1999, 48, pp. 711-718.
Dionex, "Acclaim polar advantage HPLC Columns," 2003, copy obtained on Jan. 22, 2015, pp. 1-8.
Esp@cenet English abstract of Japanese application No. JP2013092520 (A) for Measurement Method and Measurement Device for Haloacetic Acid.
Esp@cenet English abstract of Chinese application No. CN20111398607 for Method for quickly detecting haloacetic acids serving as disinfection byproducts in drinking water.
PCT/US2017/020997, ISR-WO, 10 pages, dated May 31, 2017.
PCT/US2012/036840, ISR-WO, 12 pages, dated Nov. 23, 2012.

* cited by examiner

METHODS AND APPARATUS FOR DETERMINATION OF HALOHYDROCARBONS

This application is a continuation of U.S. patent application Ser. No. 14/819,454, filed on Aug. 6, 2015, for "Methods and Apparatuses for Determination of Halohydrocarbons" (issued on Jul. 10, 2018 as U.S. Pat. No. 10,018,567). In turn, U.S. patent application Ser. No. 14/819,454 is a continuation of U.S. patent application Ser. No. 13/640,312, filed on Oct. 9, 2012 (issued on Sep. 15, 2015 as U.S. Pat. No. 9,134,290), which is a national stage entry under 35 U.S.C. § 371 of PCT Application No. PCT/US11/32438, which claims priority to U.S. Provisional Application No. 61/326,717, filed on Apr. 22, 2010. Each of the aforementioned applications names a first inventor of Harmesh K. Saini, and each of the aforementioned applications is hereby incorporated by referenced.

The present invention relates to measurement of halohydrocarbons in aqueous solutions. More particularly, this disclosure provides methods and devices that can be used for on-line measurement of trihalomethanes (THMs) in water, based on a modified Fujiwara-type reaction.

BACKGROUND

Potable water producing utilities disinfect the water by the addition of halogenating agents (halo is a prefix for chlorine, bromine and iodine). While these agents are beneficial to killing illness bearing microorganisms, they unfortunately also produce various halogenated disinfection by-products (DBPs) such as trihalomethanes (THMs), haloacetic acids, haloaldehydes, haloacetones, haloacetonitriles and chloral hydrate. THMs, in particular, head the USA EPA list of toxic and carcinogenic compounds highly regulated in drinking water. THMs as a group include chloroform ($CHCl_3$), bromodichloromethane ($CHBrCl_2$), dibromochloromethane ($CHBr_2Cl$) and bromoform ($CHBr_3$). These 4 THMs are included among the 25 volatile organic compounds regulated under the Safe Drinking Water Act (SDWA) of 1974.

In 1979, the US Environmental Protection Agency (EPA) set the maximum total contaminant level of 100 parts per billion (ppb) for the 4 THMs. The Stage 1 Disinfectant and Disinfection Byproduct Rule announced in 1998 updates and supersedes the 1979 regulations for total trihalomethanes by lowering the total THMs regulatory limit to 80 ppb. Recently the American Water Works Association (AWWA) data base reported that a safety margin of 15% below the regulatory limit for total THMs should be targeted. The Safe Drinking Water Act (SDWA) in 1996 requires the EPA to develop rules to balance the risks between microbial pathogens and disinfection byproducts (DBPs). It is important to strengthen protection against microbial contaminants, and at the same time, reduce the potential health risks of DBPs.

Subsequently, various methods and apparatus were developed for the measurement of halohydrocarbons, especially THMs, in aqueous solutions. Traditional analytical methods used to quantify THMs in water are based upon gas chromatography (GC) equipped with an electron capture detector (ECD) or a mass-spectrometer (MS). In this method, water samples are typically collected in vials and brought to an offsite laboratory to analyze by GC-ECD or GC-MS. Individual compounds are determined and the sum of all 4 THMs constitute total THMs (TTHM). This process is very laborious and time consuming.

In the literature, a simpler chemical method cited to determine total THMs in water is based upon colorimetric determination. In this method, when pyridine is reacted with THMs in a strong alkaline solution, a red color is formed. The intensity of the color is determined using an optical spectrometer. The color intensity produced is proportional to the total amount of THMs present in the sample. This method is called the "Fujiwara reaction" (K. Fujiwara, Sitzfer, Aohandl. Naturforsch. Ges. Rostock, 6, 33, 1941; G. A. Lugg, Anal. Chem., 38, 1532, 1982; T. Uno et al. Chem. Pharm. Bull., 30, 1876, 1982).

Fujiwara reactions can, however, present certain problems, as pyridine can be insoluble in some reagents used to make the medium alkaline. For example, when using an inorganic base such as NaOH or KOH, it is difficult to diffuse $OH^-$ ions from the aqueous phase into the pyridine organic phase. Since the diffusion of $OH^-$ ions is difficult to control, the results are not easily reproducible.

Most of the above methods and apparatus described in the literature for measurement of halohydrocarbons require expensive equipment, itself with substantial maintenance demands, extensive personnel training, and significant turn-round time (12-24 hours), or expose the operator to noxious chemicals. The present invention addresses the need for a low cost, simple, reliable, automated and on-line real-time method to measure THMs in water.

SUMMARY OF THE INVENTION

This disclosure provides a low cost, simple, reproducible, on-line, real-time method and apparatus to measure halohydrocarbons, particularity THMs, in an aqueous solution. The disclosed techniques are based upon an improved chemistry for a reproducible Fujiwara-type reaction, i.e., via a modified Fujiwara reaction.

One objective of the present invention is to modify the chemistry to overcome the deficiencies of the basic Fujiwara reaction. The main constituent of the traditional Fujiwara reaction is pyridine. In the embodiments presented below, a pyridine derivative is instead used; this derivative can be selected from a group of substituted pyridines (e.g., on $C_1$-$C_5$, including nicotinamide and its derivatives, alkylpyridines, azapyridines and quinoline derivatives). Ideally, the reaction chemistry is selected to minimize the odor and exposure concerns of pyridine, as in the traditional Fujiwara reaction. The pyridine derivative can optionally be dissolved into a suitable solvent, such as alcohols (butanol is a suitable example), acetonitrile, or ethers such as THF. The Fujiwara reaction can be further modified by mixing an organic base and water to form a one-phase reaction solution, increasing reliability of the results. The organic base can if desired be selected from the group of tetraalkylammonium hydroxides, including methyltributylammonium hydroxide, tetramethylammonium hydroxide, tetrabutylammonium hydroxide and tetrapropylammonium hydroxide.

Another purpose of this disclosure is to provide an improved implementation of the Fujiwara process, specifically by optimizing the timing of two (or more) absorbance measurements, for the purpose of measuring the chloroform concentration and the total THM (TTHM) content in a water sample. A method is disclosed whereby the individual concentrations of all four THM components in a potable water sample can be determined, enabling sophisticated control processes, tracking, diagnostics, alarms and other processes.

Further aspects of the invention provide a device that can be installed in-situ to periodically and automatically measure halohydrocarbon presence in a test sample, for example, a municipal water supply. The results can be automatically logged into a database for monitoring, compliance or other purposes, and can be transmitted if desired over a network (such as the internet) to a central control or reporting station, for example, that monitors multiple such devices.

Further aspects of the described technology will become clear from the description below.

DETAILED DESCRIPTION

In several of the embodiments presented in this disclosure, halohydrocarbons can be measured in four steps: 1) extracting an on-line sample and purging out volatile halogenated hydrocarbons from the sample with air or nitrogen—the purge gas may be used to carry analytes of interest over a porous absorbent surface; 2) recovering concentrated analytes from the adsorbent surface using one of several alternative processes, such as using heat (thermal desorption) or solvent (elution), to transfer the concentrated analytes into a chemical mixture (e.g., into a reaction medium); 3) causing a Fujiwara-type reaction—as mentioned, the specific reaction used involves several modifications to the traditional Fujiwara process; 4) reading the optical absorbance of the red color formed by the chemical reaction of THMs in the reaction mixture to quantify THM concentration(s).

The measurement of halohydrocarbons can be important in many contexts, among them regulation of a potable water supply, such as a municipal water supply. The embodiments presented in this disclosure facilitate a device and related method that can be use for in-situ measurement of halohydrocarbons, that is, without requiring special personnel training or experience normally associated with manual field usage of a mass-spectrometer or electron-capture detector or other sophisticated equipment. Through the use of a modified Fujiwara-type reaction, that is one that uses a pyridine derivative instead of pyridine and, optionally, a single-phase reaction, the embodiments presented herein provide a system that can be repeatedly cycled with little maintenance and with reduced exposure to noxious fumes and hazardous chemicals, and with relatively greater accuracy and reliability. As the embodiments presented herein can be used in-situ, under control of an electronic control system (e.g., a computer), these embodiments facilitate (a) a remote monitoring system (e.g., via a local area network or "LAN," or over the internet, with results reported to a central monitoring system), and (b) consequent greater accuracy and improved data retention for compliance and monitoring purposes.

Figure 1:
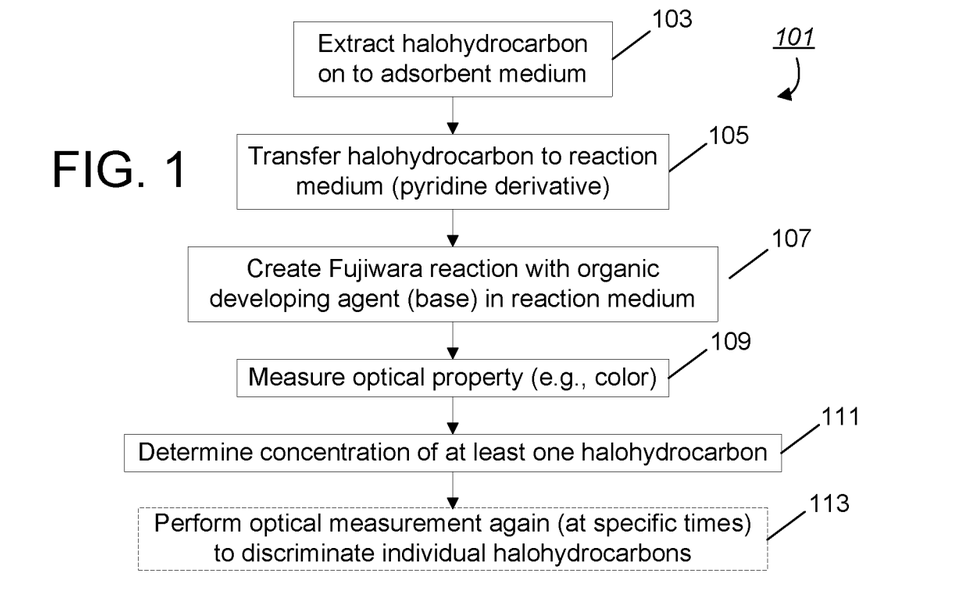
FIG. 1 provides a block diagram of an embodiment 101 of a method and system for measuring halohydrocarbons using a modified Fujiwara reaction.

FIG. 1 provides a block diagram of an embodiment 101 of a method and system for measuring halohydrocarbons using a modified Fujiwara reaction. A sample is first processed to extract at least one halohydrocarbon to an adsorbent medium, as indicated by step 103. After being concentrated on the adsorbent medium, the halohydrocarbons are transferred to a reaction medium having a pyridine derivative, as referenced by numeral 105. In addition to the pyridine derivative, the reaction medium may be an organic solution used to elute the analytes from the adsorbent medium (such as acetonitrile). Alternatively, the analytes may be removed by a thermal desorption process, such as by heating the adsorbent medium to a point where the analytes become volatile, and then sweeping the volatile analytes into the reaction medium using gasses such as nitrogen or air. As depicted by reference numeral 107, the analytes are subjected to a modified Fujiwara reaction, based on an organic developing agent (such as the hydroxide of an organic cation) and an optional organic solvent, at a controlled, elevated temperature (e.g., present in the medium mentioned earlier). As the reaction proceeds, the color intensity of the reaction medium changes, and this optical property is measured during the reaction, per numeral 109. Based on the measured optical results, halohydrocarbon concentration is determined, as indicated by reference numeral 111.

In fact, there may be several halohydrocarbons (e.g., THMs) present in unknown quantities, and the system of FIG. 1 may therefore optionally be applied to discriminate between the THMs and to determine their individual concentrations. As indicated by dashed-line (i.e., optional) process block 113, the optical properties of the reaction medium may be measured two or more times, at different times, to detect the change in color intensity. As will be presented below, based upon predetermined data, total THM presence may be determined and individual THM concentrations determined from this data based on on-line or real-time measurements.

Figure 2:
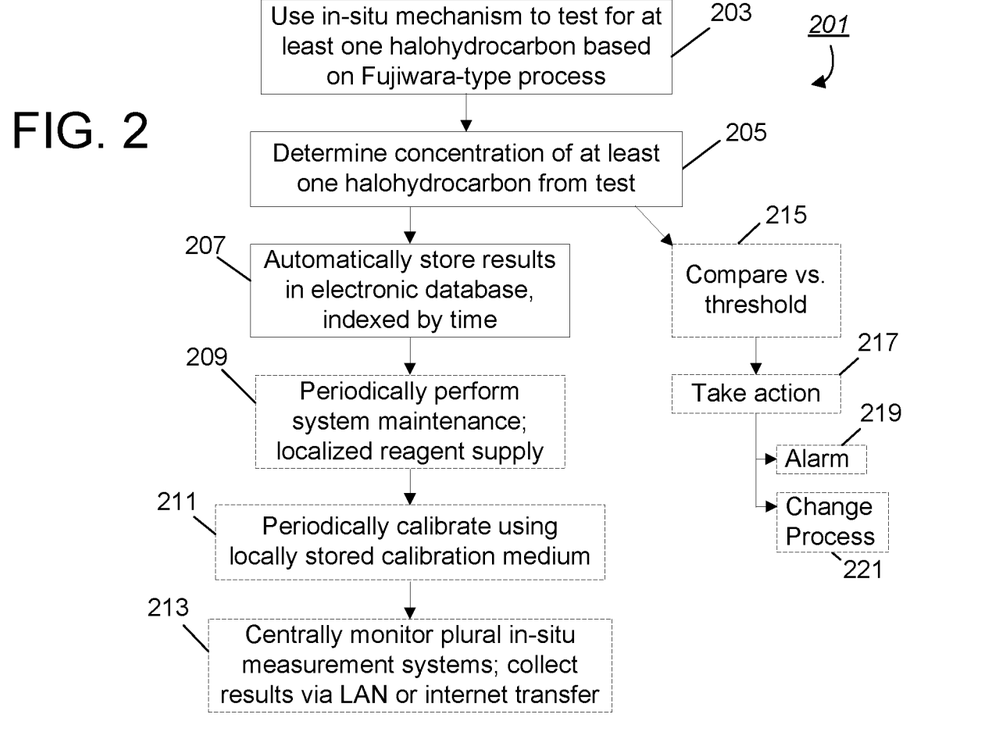
FIG. 2 provides a block diagram of an embodiment 201 that uses an in-situ mechanism to monitor halohydrocarbon presence. As represented by dashed lines, the embodiment may optionally feature in-situ maintenance and calibration using local storage for reagents, fluids and other materials used in operation of the system; additionally, the in-situ mechanism may be part of a remote monitoring system that monitors a network of several such mechanisms.

FIG. 2 introduces a system embodiment 201, including a business method, which may rely on the embodiment of FIG. 1. In particular, an in-situ apparatus may be used to test for at least one halohydrocarbon, based on a modified Fujiwara process as just described and as reference by numeral 203. Because a modified chemical process is used, including optional automation, the system may be performed in-situ and may help limit worker exposure to noxious fumes or hazardous chemicals, and provide greater accuracy relative to phase-separated reactions. Based on the measurements, concentration of at least one halohydrocarbon is determined (per numeral 205). The results may be electronically stored in a database, indexed by time, thereby serving the compliance goals referenced above, e.g., a log may be generated and kept to show compliance and to track situations and times when detected substances exceed desired levels, as alluded to by numeral 207.

FIG. 2 also references several optional steps. First, the use of pyridine derivatives and relatively safe chemicals facilitates local maintenance, e.g., materials used for the reaction may be stored in local reservoirs and occasionally replenished, with waste materials being collected and safely disposed. Relatively easy maintenance facilitates in-situ systems without requiring extensive training of personnel. Second, materials that degrade over time may be recalibrated and used until they need to be replaced using one or more locally stored calibration media (i.e., one or more "standards"); as will be presented below, for example, an electronic control system may be used to run the same steps used to test the potable water supply with each locally stored calibration test medium (e.g., on THM-free water); self-calibration further enhances the ability to provide and effectively use in-situ devices for monitoring chemicals such as THMs. Finally, for embodiments that use computer control of the various sampling and testing steps according to a predetermined schedule, a LAN or internet connection may also be provided for transmitting measurement results to a central monitoring facilities, e.g., a regulatory agency, regional water management station, or some other type of entity, thereby providing for enhanced ability to continuously monitor chemical levels and quickly respond to problems. In this case, data from the particular in-situ machine can be indexed by various factors, including time of measurement, particular THM values, an identifier of the particular machine that produced the data, location, etc. This data may be logged either in a dedicated file, or as part of a database used to track several of the on-line mechanisms. These options are variously indicated by numerals 209, 211 and 213 in FIG. 2. If desired, the determination of THM amounts may be compared to one or more thresholds, as indicated by dashed line "options" block 215, with action (217) being responsively taken depending on this comparison. An alarm (219) may be generated if THM concentrations exceed desired level; alternatively, an electronic control system may responsively and automatically adjust upstream water treatment processes, either by increasing or decreasing the use of certain chemicals, to provide for a sanitized water supply without exceeding recommended THM norms, as collectively represented by block 221. Individual THM species contributions may also be used in diagnosing issues associated with the water treatment process.

With several principal features of the present disclosure thus introduced, additional detail will now be presented, with reference to FIGS. 3-10.

Figure 3:
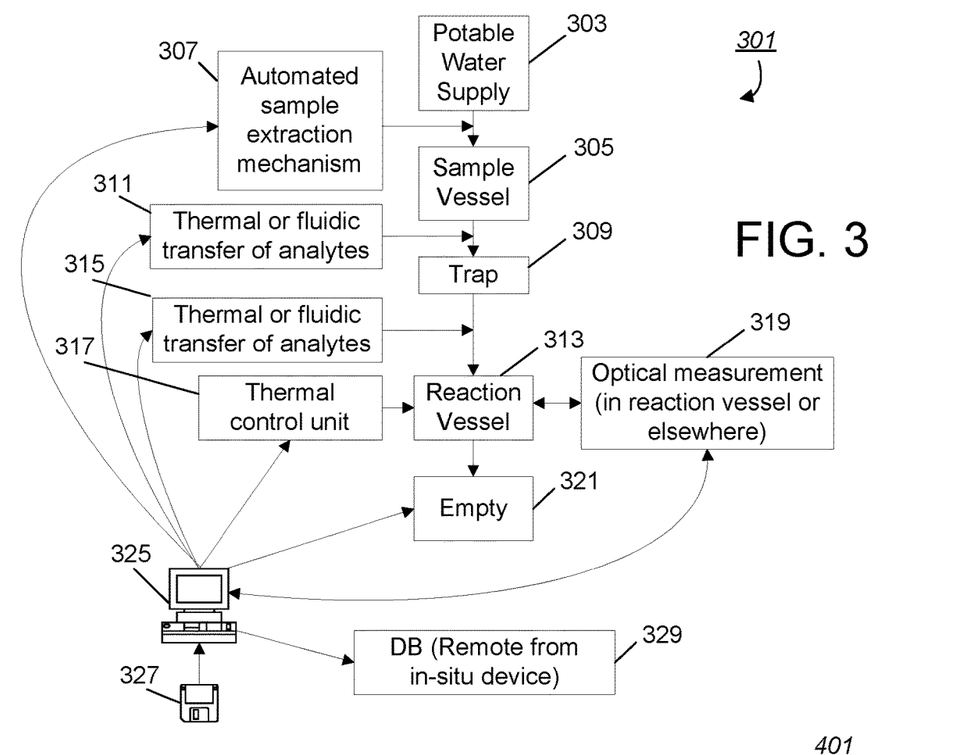
FIG. 3 provides a block diagram of an embodiment 301 of a system or device for measuring halohydrocarbons, THMs in particular.

FIG. 3 presents a block diagram of an embodiment 301 of a system or device that may be used for in-situ measurement of halohydrocarbons. In particular, a potable water supply 301 is to be monitored to periodically determine the presence of halohydrocarbons. In one embodiment, monitoring may occur taken at frequent intervals, for example, every hour, around the clock. The water supply 303 may be for example a particular point in a municipality's or water company's distribution network. At each monitoring interval, a sample may be extracted from the potable water supply and transferred to a vessel 305. The sample extraction may be part of an on-line mechanism 307 that automatically draws a predetermined volume of water into the purge vessel. Halohydrocarbons are then extracted from the water test sample and transferred to a column trap 309, which contains the adsorbent medium previously referred to (e.g., a porous medium). This extraction may be accomplished by passing gas through the water test sample, and adsorbing the analytes extracted by the gas to the adsorbent medium, as indicated by numeral 311, or by directly passing the test water through that medium. Once the processing of the test water sample is complete, the now-concentrated analytes are again transferred, using a thermal or fluidic transfer process, to a reaction vessel, per numeral 313 and 315. As indicated earlier, a fluidic process may use a solvent to flush the analytes from the adsorbent medium, and an alternative thermal process may simply heat the analytes, and pass them through a reaction medium (e.g., organic solvent), to force the analytes into solution at room temperature. When the proper reaction mixture is ready (i.e., the reaction medium, post introduction of a pyridine derivative and organic developing agent, such as an organic base), the single-phase mixture or medium is then heated in a controlled manner which causes the reaction to progress; a thermal control unit 317 may be used for this purpose. The reaction produces a color that changes in intensity dependent upon the time of the reaction, the temperature and the concentrations of the halohydrocarbons present in the reaction medium; the intensity change is optically measured, for example, by determining the optical transmission through the reaction medium at a specific wavelength, and an optical measurement device (e.g., an optical spectrometer) may be used for this purpose, as indicated by 319. At one or more times as the reaction proceeds, the optical measurement may be repeated, with the time and transmission at the specific wavelength used to determine chloroform and total THM presence. Once the last measurement has been taken, the reaction well can be emptied, per numeral 321, and the system can be prepared for testing at the next monitoring interval, as indicated by numeral 329.

FIG. 3 also illustrates a computer 325, control software 327, and a number of control arrows to show that the computer can act as an electronic control system for automating the steps (and associated timing) of each of the elements referred to above. Specifically, the computer can be controlled according to a predetermined time schedule or remotely, on a dynamic basis, to automatically perform testing steps from test sample extraction, from to THM calculation to system cleaning, all without human intervention. If desired, optical test results can also be relayed to a remote location, with THM concentration calculation being remotely performed.

As indicated, one feature of embodiments presented in this disclosure is the use of a modified chemical process to overcome the deficiencies of the basic Fujiwara reaction. The main constituent of the traditional Fujiwara reaction is pyridine. In the embodiments discussed above, a pyridine derivative is selected from a group of other substituted pyridines, including nicotinamide and its amide-alkylated derivatives, and alkylpyridines such as 3-picoline. The reaction chemistry does not share the strong odor of pyridine, as in the basic Fujiwara reaction, and is safer to use. Suitable criteria for selecting a pyridine derivative include identifying a material that (a) is based on a pyridine ring structure with one or more of the hydrogen atoms in the ring structure replaced, (b) possesses less noxious characteristics (smell, hazardous exposure) of pyridine, (c) is not volatile, (i.e., has a boiling point greater than the associated reaction temperatures, e.g., greater than 80° C.), and (d) is consistent with proper progression of the Fujiwara-type reaction, that is, the reaction induces a color intensity change in reaction with halohydrocarbons. The pyridine derivative can be dissolved into an organic solvent such as methanol, butyl alcohol, or acetonitrile. The basic Fujiwara reaction can be further modified by mixing an organic base and water to form a one-phase reaction solution. In one embodiment, the organic base is selected from the group of tetraalkylammonium hydroxides including methyltributylammonium hydroxide, tetramethylammonium hydroxide, tetrabutylammonium hydroxide and tetrapropylammonium hydroxide.

Figure 4:
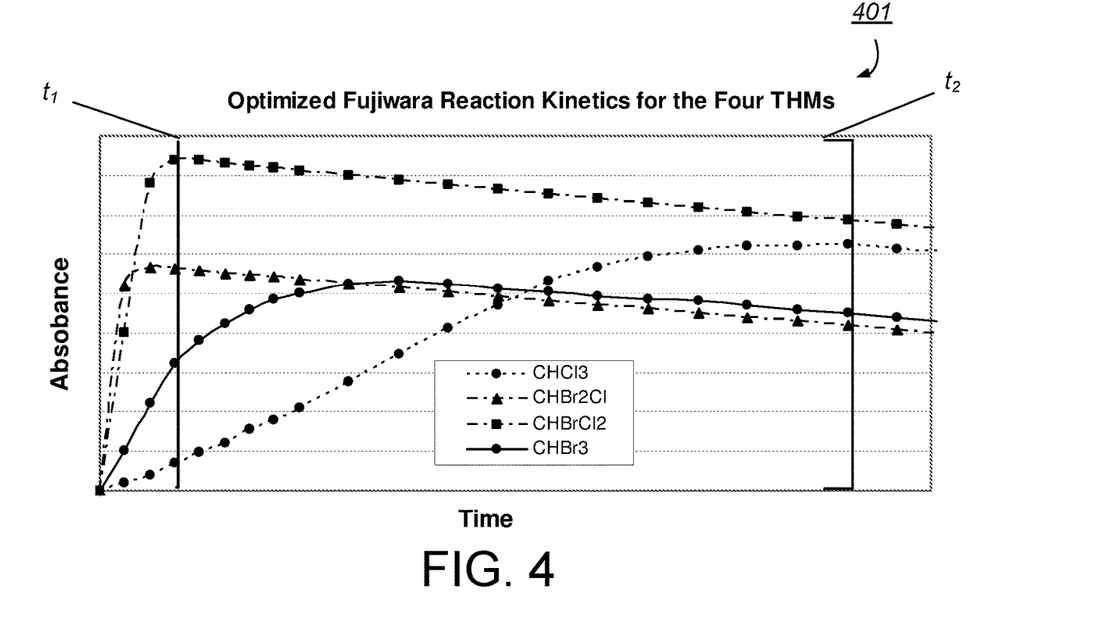
FIG. 4 is a graph 401 used to explain computation of concentration of individual THMs, based on two time-based optical absorbance measurements.

The composition of the reagent mixture, reaction temperature and timing can be carefully selected to improve the method by making a determination of the concentrations of the four individual THM components (as well as their total). This modification to the basic chemical method takes advantage of the different reaction kinetic and equilibrium profiles for the four THMs. That is, as part of the Fujiwara-type reaction, the four THMs are converted to a colored product at different rates and to different extents of formation. For example, when a pyridine derivative such as 3-picoline is mixed with the solvents acetonitrile and water and treated with an organic base such as tetramethylammonium hydroxide, then the reaction profiles can be followed by monitoring the time resolved absorption of the product, as depicted in FIG. 4. As can be seen, the color development from the reaction of the two mixed bromo-chloro THMs reaches a maximum early at $t_1$ (represented by a left-most vertical line within the area of the graph 401). In contrast, chloroform reacts most slowly, with the colored solution becoming most intense at time $t_2$ (represented by a right-most vertical line in FIG. 4). In principle, four measurements of the development in color of a THM/Fujiwara chemical reaction mixture could be used to deconvolute the absolute concentrations of the four individual THM components or species referred to earlier. This process will be further explained below with reference to FIGS. 7-9.

Another feature of the method and embodiments presented in this disclosure is the use of two calibration standards for the purpose of maintaining accuracy and repeatability in the determination of the speciation of the four THMs in the water samples. A particularly beneficial set of calibration standards is comprised of one containing only $CHCl_3$, and another formulated with a mixture (not necessarily in equal proportions) of the three brominated THMs ($CHCl_2Br$, $CHBr_2Cl$ and $CHBr_3$). This strategy takes advantage of the information taught in FIG. 4, which demonstrates that an early absorbance at time $t_1$ most significantly corresponds to the quantitative sum of the three brominated THMs, whereas the absorbance measurement at time $t_2$ reflects the concentration of all four THM components. Alternatively, a separate standard may also be used for each brominated THM. In the act of calibrating the modified Fujiwara process in the disclosed apparatus, two time-resolved absorbance results (at $t_1$ and $t_2$) for each of the two calibration standards at known concentrations are measured and recorded (for example in a database). These four time-resolved absorbance values are the coefficients necessary to construct the calibration "curves" of the Beer-Lambert Law which relates absorbances to concentrations. Thus for an unknown sample of mixed THMs, the concentrations of $CHCl_3$ and the TTHMs can be calculated by mathematical solving a set of two simultaneous equations based on two input variables (absorbance measurements at times $t_1$ and $t_2$) and the set of known absorbance values.

The measurement methodology can be further improved to solve for all four THM concentrations by taking into consideration the premise that the relative speciation of the four THMs is a natural function of the kinetics of their formation in the water disinfection process (depending on parameters such as the concentration and type of organic matter in the water, pH, temperature, chlorine dosage and bromide levels in the water). This principle is depicted graphically in FIG. 7, which represents the relationships between the speciation of the four THMs derived from measurement of 40 drinking water samples collected from water utilities geographically dispersed in the UK. For example, it is observed for most disinfected drinking water samples whose $CHCl_3$ level contributes 30% to the total THM value (represented by the left-most vertical line in FIG. 7), that the relative amounts of $CHCl_2Br$, $CHBr_2Cl$ and $CHBr_3$ are typically close to 35%, 28% and 7% respectively. Similarly, if the $CHCl_3$ level is 60% of the total THM levels in water samples (see the right-most vertical line in FIG. 7), the same other components are expected to be 27%, 12% and 1% in relative proportions.

By taking advantage of this natural speciation profile of THMs in drinking water samples, a method for the deconvolution of all four THM components can be achieved based on as few as two different time-based absorbance measurements during the Fujiwara-type reaction; the first measurement is performed at a relatively early stage ($t_1$) and the second at a later time ($t_2$) (again, these are represented by the vertical lines within the graph area of FIG. 4). Thus, in at least one embodiment, the halohydrocarbon measurement techniques discussed above are repeated twice for the purposes of identifying concentration of each THM species or component, as referenced above, based on time-dependent curve data as presented in FIG. 4. The optical measurements obtained at each time are linked to the horizontal axis in the graph of FIG. 4 (based on elapsed time since the reaction commenced), and the concentration of individual THM components are determined from total chloroform and total "group" THM determinations.

This analytical and computational technique for the determination of the speciation of THMs in drinking water, based on two absorbance measurements in a modified Fujiwara reaction mixture on an apparatus calibrated in the above manner, has been demonstrated to be reliable over a wide range of THM speciation. For example, a heavily chlorinated prepared mixture of THMs equivalent to a water sample at a total THM concentration of 75.5 ppb (comprising 64.7 ppb $CHCl_3$, 9.9 ppb $CHCl_2Br$, 0.8 ppb $CHBr_2Cl$ and 0.1 ppb $CHBr_3$) was determined after 20 measurements to contain an average TTHM value of 74.6 ppb (−1.2% accuracy and 0.5% RSD) and 86% $CHCl_3$ (64.2 ppb $CHCl_3$; −1.5% accuracy and 0.7% RSD). At the other end of the spectrum of THM speciation in drinking water, a heavily brominated mixed THM sample equivalent to a total THM concentration of 53.3 ppb in water (9.5 ppb $CHCl_3$, 21.4 ppb $CHCl_2Br$, 14.9 ppb $CHBr_2Cl$ and 7.5 ppb $CHBr_3$) was determined after 20 measurements to contain an average TTHM value of 53.8 ppb (+1.0% accuracy and 0.8% RSD) and 17% $CHCl_3$ (8.9 ppb $CHCl_3$; −6.5% accuracy and 2.9% RSD).

More specific implementations of an in-situ device, can operate as follows:
  a) the system purges a test sample at an elevated temperature, preferably 60-70° C., to separate volatile hydrocarbons, including THMs, from bulk sample volume;

b) the system then concentrates halohydrocarbons from a very dilute sample onto an adsorbent trap material, enhancing sensitivity and reducing bias; In one embodiment volatile hydrocarbons, preferably THMs, are by this process continuously adsorbed on a porous surface of carbopack and carboxen layers (trap), or the porous surface medium can be derived from of 2,6-diphenylene oxide;

c) volatile hydrocarbons, preferably THMs, are then quantitatively desorbed from the trap by heat (thermal desorption) or quantitatively eluted with solvent from the porous surface (solvent elution) into the reaction medium (i.e., a reaction mixture);

d) halohydrocarbons react with reaction mixture at elevated temperature and form red color species; and e) measurements are then made of the optical absorption of this red color species to determine halohydrocarbon concentrations in aqueous sample.

These features can be automated, e.g., performed under computer control with the entire measurement (and subsequent cleaning process) taking less than one hour (e.g., it will be recalled that in one embodiment, new measurements are taken at intervals of every hour). The base processes referred to above can be performed more quickly and thus, in another embodiment, the entire process can be completed in as little as 15 to 20 minutes, or even more quickly.

Two such embodiments are discussed with reference to the attached FIGS. 5 and 6.

Figure 5:
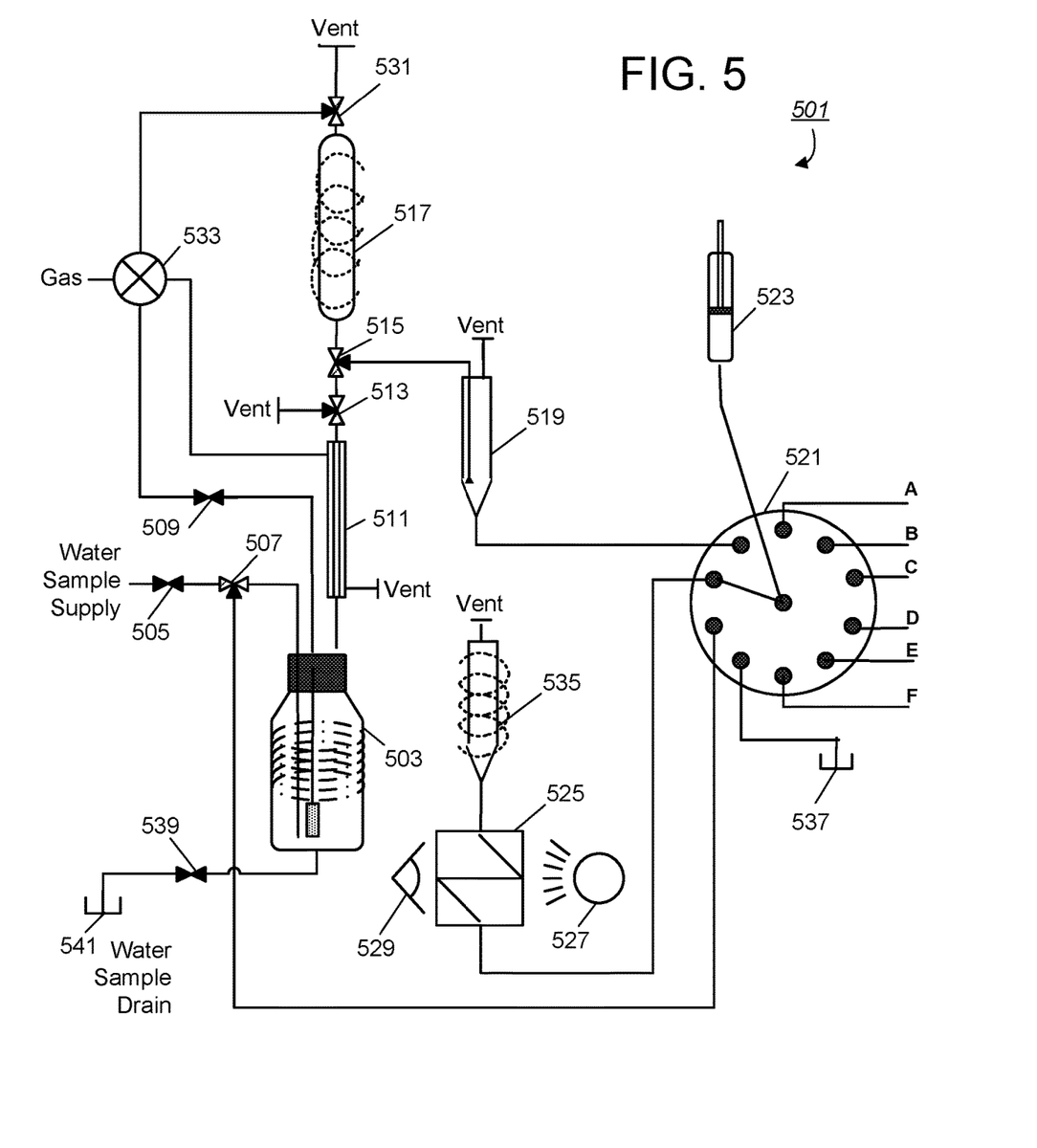
FIG. 5 provides an embodiment 501 of an in-situ device for measuring halohydrocarbons, for example, an on-line device for measuring halohydrocarbon presence in potable water, on a real time basis.

FIG. 5 is a schematic of one embodiment 501 of an in-situ analytical device. During operation, a water sample enters a vessel 503, via a two-way valve 505 and three-way valve 507 to a preset volume enforced by a level sensor (the sample amount is specified depending upon the required detection limit and historic makeup of the sample). The water sample is heated in vessel 503 to a predetermined temperature setting to facilitate release of the volatile halohydrocarbons. The air or nitrogen gas from two-way valve 509 is then bubbled through the sample. Air or nitrogen gas then carries volatile halogenated hydrocarbons through a dryer 511, where any moisture in the gas is removed. Gas passes through two three-way valves 513 and 515 and enters into a trap (column) 517 that contains layers of material that adsorbs volatile halohydrocarbons, such as THMs. The gas then is vented after passing through valve 531. Then, valve 515 is opened toward a chemical reservoir 519. Using a rotary selector valve 521, a predetermined amount of pyridine derivative reagent A and the optional organic solvent B is introduced to the reservoir 519 by an electronically-controlled syringe 523. Syringe 523 then sends the solution into a flow cell 525 of an optical spectrometer. Light from a light source 527 passes through the solution in the flow cell while a detector 529 measures the intensity of the transmitted light. The measurement taken from this solution is called a "blank" reading. The solution is pulled back to the syringe 523 and then pushed to the reservoir 519.

The trap (column) 517 is then heated to a temperature suitable for volatilizing the analytes and air or nitrogen is swept through the column. This causes the halogenated hydrocarbon to be desorbed from the column and bubbled into solution in the reservoir 519. The path followed by low-pressure air or nitrogen is from a regulator 533, through the column and to the reservoir 519 via valve 515. At the end of desorption, the solution which contains halogenated hydrocarbons and an organic reagent C is drawn back to the syringe 523 and is mixed well. The reaction medium in the reservoir 519 at this point contains the pyridine derivative A, the optional organic solvent B, the strong organic base C, and the halohydrocarbons (in unknown quantities).

The reaction mixture is then pulled into syringe 523 via the rotary selector valve 521 from the reservoir 519. The solution from the syringe 523 is pushed to a heated reservoir or reaction vessel 535, where the temperature is fixed (a particularly useful range is 70-80° C.). The solution stays in the reaction vessel for a predetermined amount of time, during which the reaction begins and progresses, activated by the consequent heating. The clear solution in the heated reservoir 535 begins to turn to the color red and, after first specified time, $t_1$, the solution is pulled back into the flow cell 525 where the solution is cooled, thereby halting the reaction. The optical intensity is then measured at time $t_1$; in one embodiment, this first reading is taken at an interval of 60 to 120 seconds following initiation of the reaction. As soon as the reading has been taken, the solution is pushed back to the reaction vessel 535 and stays there again for another specified amount of time. The solution is then once again pulled back to the flow cell where the solution is again cooled before a second intensity measurement is taken at time $t_2$; again, in one embodiment, this second reading is taken at an interval of 600 to 1200 seconds after initiation of the reaction. The solution is then drawn back to the syringe 523 and sent to a chemical waste drain or container 537 through a port of the rotary selector valve 521.

Two absorbance values at times $t_1$ and $t_2$ are calculated using the optical transmission measurements represented by the blank reading and the measurements taken at times $t_1$ and $t_2$. These two absorbances are used to determine two concentrations of halogenated hydrocarbons, specifically chloroform and the total THM in the unknown on-line water samples in the manner presented above.

The system is returned to a ready state by routine cleaning maintenance. The water sample in the purge vessel 503 is emptied by applying pressurized air or gas through valve 509, and opening the valve 539 to the waste water drain 541. The components employed in the chemical reaction, specifically the flow cell 525, the syringe 523 and the reservoirs 519 and 535, are cleaned with either the organic solvent B, or a dedicated cleaning reagent (such as THM-free water or another agent) D. The trap 517 is treated to a bake process at an elevated temperature (such as 240° C.) and swept with gas/air from regulator 533, through valves 531 and exiting out the vent of the reservoir 519.

The analytical system embodiment just presented has the capability to introduce standards for the calibration and validation of the process. In the case of THM determination, one standard E is for chloroform and another standard F is for the three brominated THMs. To perform an on-line calibration, the vessel 503 is filled with a known amount of THM-free water (e.g., distilled water, or water purged free of THMs with air through valve 509 and vented out valve 513). A known concentration and amount of chloroform standard E and/or brominated standard F is added to the vessel 503 via valve 507 by syringe 523 drawn through the rotary selector valve 521. The process set up is as described earlier. The absorbances of the red color of the calibration reaction solution at times $t_1$ and $t_2$ are recorded and absorbance values are constructed from the slopes of the concentration vs. absorbance relationships. This calibration slope may be used to quantitatively determine the concentration of halohydrocarbons in unknown on-line water samples in the manner presented above.

Figure 6:
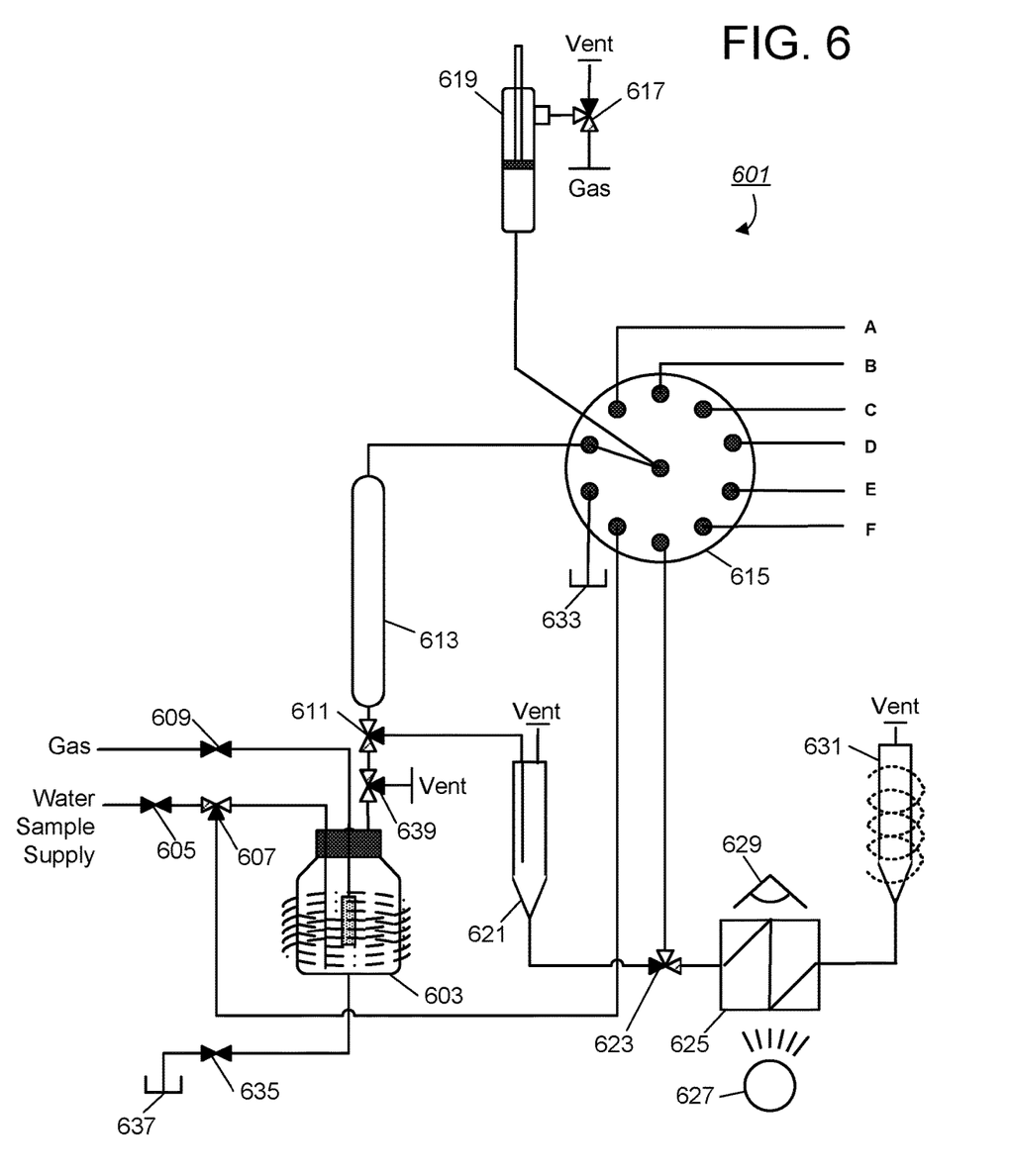
FIG. 6 provides an embodiment 601 similar to the embodiment seen in FIG. 5.

FIG. 6 is a schematic of another embodiment 601 of an analytical system which halohydrocarbons are concentrated on a porous material and eluted with solvent.

During operation, a water sample enters a vessel 603, via a two-way valve 605 and the three-way valve 607. The sample in vessel 603 is heated to a predetermined temperature setting. Air or nitrogen gas from two-way valve 609 is bubbled through the sample. The gas then carries the volatile halogenated hydrocarbons through three-way valves 639 and 611 into a packed column 613 containing layers of adsorbent material to adsorb volatile hydrocarbons, such as THMs. This purge gas passes through a port of a rotary selector valve 615, and vented through valve 617 connected to an opening in the syringe 619. After an appropriate time for the purge transfer of the halohydrocarbon analytes from the water sample to the trap column 613, valve 611 is then opened toward the chemical reservoir 621.

Using the rotary selector valve 615, a predetermined amount of organic solvent B, such as acetonitrile, is drawn into an electronically-controlled syringe 619 and transferred through the column 613. The halogenated hydrocarbons are quantitatively eluted from the column and collected in the reservoir 621. A fixed amount of pyridine derivative A is mixed into the reservoir 621 with syringe 619 through ports of the rotary selector valve 615 and valve 623. The solution is then mixed by pulling the solution to the syringe 619 and then pushing the solution back to the reservoir 621. The organic solvent with halogenated hydrocarbons and pyridine derivative is then drawn back to the syringe 619 and sent to a flow cell 625. The light from a light source 627 passes through the solution in the flow cell 625 while a detector 629 measures the intensity of the transmitted light. The measurement taken from this solution is, once again, called a "blank reading." The solution is pulled back to the syringe and pushed to back to the reservoir.

For the ensuing reaction-dependent measurements, the reaction mixture is pulled into the syringe 619 via the rotary selector valve 615. A fixed amount of the base reagent C is introduced into syringe 619 and the solution is mixed well. The reaction medium in the syringe at this point contains the organic solvent B, pyridine derivative A, the strong organic base C, and the halohydrocarbons (in unknown quantities). The solution is pushed into a heated reservoir or reaction vessel 631, where the temperature is fixed at a predetermined point (a particularly useful range is 70-80° C.). The solution stays in the reaction vessel for a predetermined amount of time. Beginning as a clear solution, under the influence of the heat, the solution begins to react and turns to red. After a first specified time, $t_1$, the solution is pulled back into the flow cell 625 where the solution is cooled, halting the reaction before the intensity measurement is taken. The optical intensity is then read out at time $t_1$. The solution is pushed back once again to the heated reaction vessel 631 and stays there again until another specified time, $t_2$. Once that second specified time arrives, the solution is again pulled back to the flow cell 625 where it is again cooled before the intensity is measured at time $t_2$. Finally, the solution is drawn back to the syringe 619 and sent to a chemical waste drain or container 633.

Two absorbances are calculated using the measured light intensities provided by the blank reading and optical measurements at times $t_1$ and $t_2$. These two absorbances are used to determine two concentrations of halogenated hydrocarbons, specifically chloroform and the total THMs in the unknown water samples in the manner presented above.

As with the embodiment of FIG. 5, the analytical system of the system of FIG. 6 is returned to a ready state by routine cleaning maintenance. The water sample in the purge vessel 603 is emptied by applying pressurized air or gas through valve 609, and opening the valve 635 to the waste water sample drain 637. The components employed in the chemical reaction, specifically the flow cell 625, the syringe 619 and the reservoirs 621 and 631, are cleaned with either the organic solvent B, or a dedicated cleaning reagent (such as THM-free water) D. The trap 613 is treated to a process that evaporates the residual solvent by sweeping it with gas/air through valves 617 and rotary selector valve 615; the hot gas is then removed through the vent of the reservoir 621, via valve 611.

As with the embodiment of FIG. 5, the analytical system of the system of FIG. 6 also has the capability to introduce standards for the calibration and validation of the process. In the case of THM determination, one standard E is for chloroform and another standard F is for brominated THMs. To perform an on-line calibration, vessel 603 can be filled with a known amount of sample water and made THM-free by purging THM using air flowing in through valve 609 and venting out through valve 639. A known concentration and amount of chloroform standard and/or brominated standard is added to the vessel by the syringe 619 drawn through the rotary selector valve 615, and in to the purge vessel through valve 607. The process set up is as described earlier. The absorbances of the red color of the calibration mixture are recorded at times $t_1$ and $t_2$, and the relationship between absorbances and known concentrations is evaluated. The resultant slope may be used to quantitatively determine the concentration of halohydrocarbons in on-line samples in the unknown on-line samples in the manner presented above.

As introduced above, some embodiments presented by this disclosure may be used to resolve individual THM species based on two or more optical measurements. This principle was introduced above by reference to FIG. 7, and is further discussed below with reference to FIGS. 8 and 9.

Figure 7:
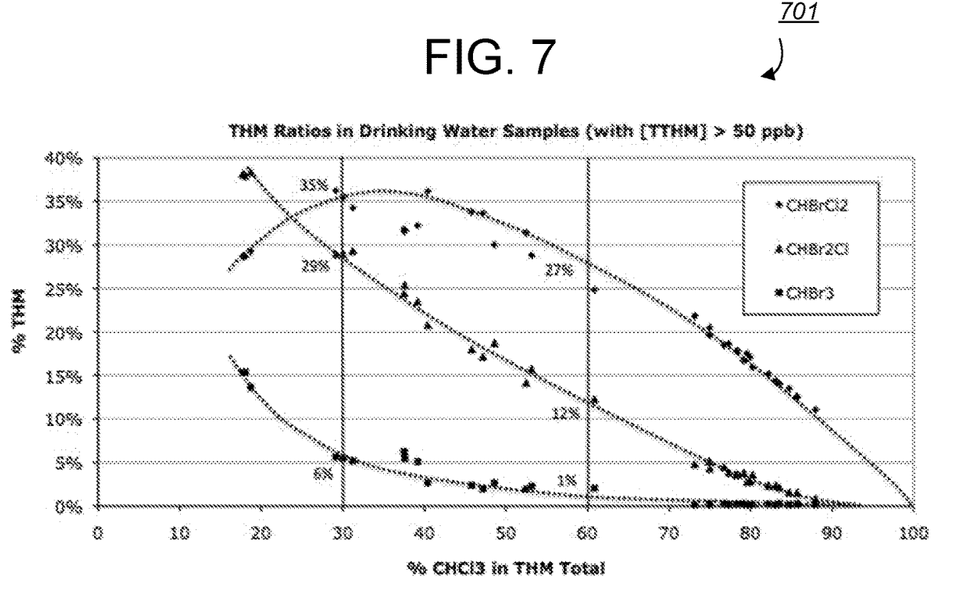
FIG. 7 is a graph 701 that depicts the relationships of the relative ratios of the four THMs measured in a historical set of 40 drinking water samples collected from several geographically dispersed water utilities in the UK.
Figure 8:
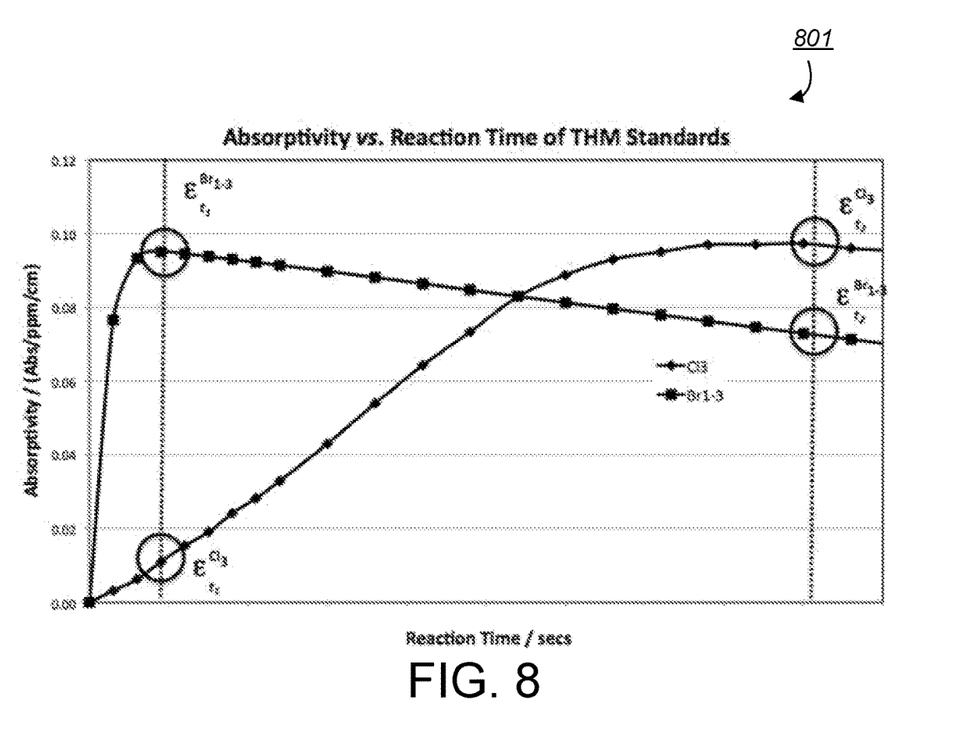
FIG. 8 is a graph 801 that depicts the time-dependent optical absorptivity coefficients of two Fujiwara reaction solutions, one containing chloroform and the other a mixture of the three brominated THMs.

As mentioned, FIG. 7 provides a sample graph 701 that depicts the relationships of the relative ratios of the four THMs, while FIG. 8 provides a graph 801 that shows absorbance variation for individual THM species in dependence upon reaction time. Through the measurement of absorbance of two different points in the reaction, concentration of each THM species can be derived from the total THM measurement introduced above, and this information can be used in conjunction with the data presented in FIGS. 7-8 to determine individual THM species concentrations. This process is explained with reference to FIG. 9.

Figure 9:
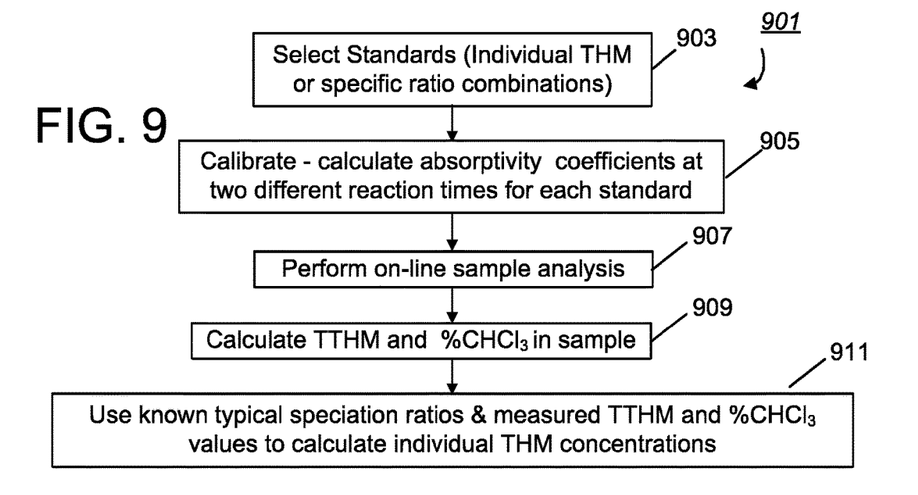
FIG. 9 is a flowchart 901 relating to calculation of individual THM concentrations based on measurements, such as those presented in FIG. 8, and expected THM ratios such as those depicted in FIG. 7.

In particular, FIG. 9 further provides a flow chart 901 illustrating steps that can be used to determine these individual concentrations.

1) Selection of Standards (903): Appropriate calibration standards of individual THMs, or alternatively, a mixture of THMs, are selected. A particularly useful two-STD configuration comprises one standard containing chloroform only (labeled 'Cl3'), and the other containing a mixture of the three brominated THMs (labeled 'Br1-3') (the ideal standards reflect the most probable composition or ratio expected in the water samples to be analyzed).

2) System Calibration (the establishment of time-dependent absorptivity coefficients for each standard) (905): Using the same in-situ device that will be used to take "real-time" samples, a known quantity of each standard is added in an independent process to a THM-free water sample in the purge vessel, and the method described above (purge/trap/desorb/reaction) is performed upon this sample, to measure absorbance at each of two reaction times $t_1$ and $t_2$. According to the Beer-Lambert Law, an absorptivity coefficient ε (epsilon) at each time is calculated: $\varepsilon_t = A/l \cdot c$ (where A=Absorbance, l=optical path length in the flow cell, and c=concentration). These values correspond to the values enclosed within the circles in FIG. 8, and are respectively labeled as $^{Cl3}\varepsilon_{t1}$, $^{Cl3}\varepsilon_{t2}$, $^{Br1-3}\varepsilon_{t1}$ and $^{Br1-3}\varepsilon_{t2}$. The values obtained are stored (e.g. in a database) for use later.

3) Sample Analysis (907): For in-line or "live" measurements, that is, to determine unknown THM concentrations in a water sample, an aqueous sample is taken (e.g., from a potable or other water supply, as described earlier) and subjected to the complete process (purge/trap/desorb/chemical reaction) to measure the two optical absorbances at time $t_1$ and $t_2$ ($A_{t1}$ and $A_{t2}$).

4) TTHM and % $CHCl_3$ Concentrations Determined (909): One then solves for the concentrations of chloroform and brominated THMs in the sample ([$CHCl_3$] and [$CHBr_{1-3}Cl_{2-0}$]) by solving the following two simultaneous equations:

$$[CHBr_{1-3}Cl_{2-0}] = (A_{t1} \times {}^{Cl3}\varepsilon_{t2} - A_{t2} \times {}^{Cl3}\varepsilon_{t1})/({}^{Br1-3}\varepsilon_{t1} \times {}^{Cl3}\varepsilon_{t2} - {}^{Br1-3}\varepsilon_{t2} \times {}^{Cl3}\varepsilon_{t1}) \quad (1)$$

$$[CHCl_3] = (A_{t1} - [CHBr_{1-3}Cl_{2-0}] \times {}^{Br1-3}\varepsilon_{t1})/{}^{Cl3}\varepsilon_{t1} \quad (2)$$

where $^{Cl3}\varepsilon_{t1}$, $^{Cl3}\varepsilon_{t2}$, $^{Br1-3}\varepsilon_{t1}$, and $^{Br1-3}\varepsilon_{t2}$ represent the stored calibration data obtained from step (2), above. The total THM concentration [TTHM] is equal to [$CHBr_{1-3}Cl_{2-0}$]+[$CHCl_3$], and the percentage of chloroform in the sample is equal to $100 \times [CHCl_3]/([CHBr_{1-3}Cl_{2-0}]+[CHCl_3])$.

5) Calculation Of Speciation Of Each Individual THM (911): To deduce the individual concentrations of the three brominated THMs in the water sample ([$CHBrCl_2$], [$CHBr_2Cl$], and [$CHBr_3$]), the values obtained for [$CHCl_3$] and [TTHM] from step (4) are compared using the information presented in FIG. 7, and used to solve for each individual brominated species.

This procedure for determining the individual concentrations of all four THM components in potable water samples can be demonstrated by applying the analysis to the two exemplary samples discussed earlier.

As can be seen from this discussion, embodiments presented herein provide a novel, automated way to calculate each individual THM species of interest. As alluded to earlier, a control system may, as part of an in-situ device, part of a local area network ("LAN") or over a wide area network ("WAN," e.g., the internet), automatically monitor a water supply and take remedial action, for example, by sounding or otherwise triggering an alarm, or by using an electronic control system and the feedback provided by periodic measurements to adjust chemical treatment upstream in a water sanitation or other process.

As mentioned, the embodiments presented in this disclosure facilitate a device that can be installed in the field near the water distribution system, that can collect and analyze samples on-line, avoiding the need to collect samples in vials and deliver them to an offsite laboratory for analysis. The system may be run continuously, 24 hours per day, unattended, with a warning indication or other action if contaminants exceed a specified limit, responsive to a detected maintenance condition, or on another ad-hoc basis.

Figure 10:
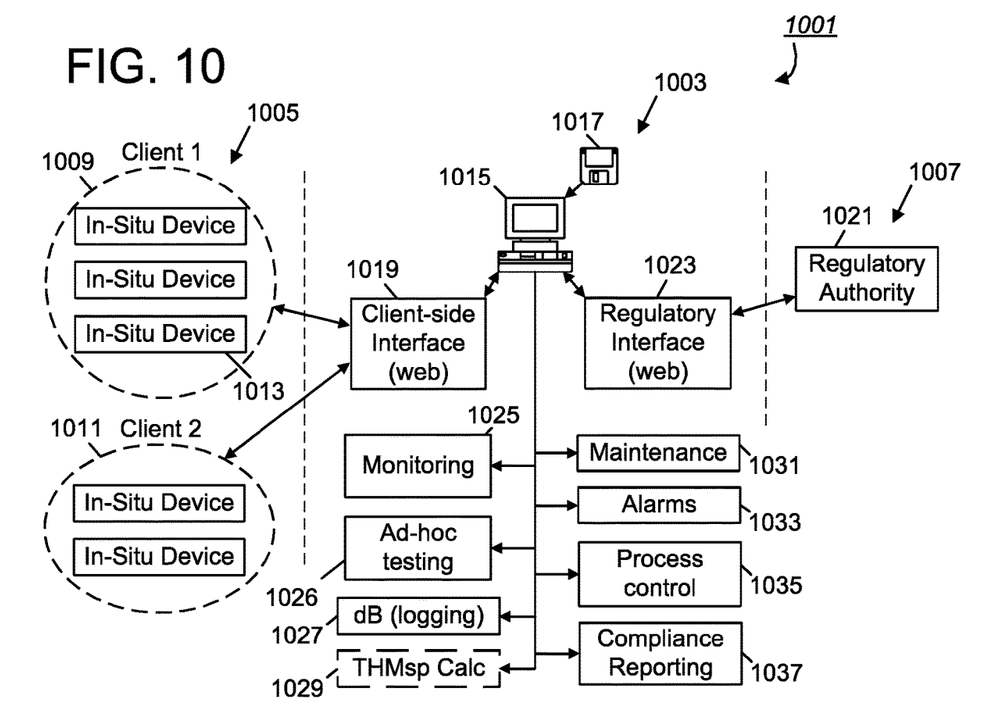
FIG. 10 is a system diagram 1001 used to explain a method of remotely monitoring one or more in-situ mechanisms.

FIG. 10 provides a system diagram 1001 used to explain a method of remotely monitoring one or more in-situ mechanisms or devices. In particular, FIG. 10 is divided into middle, left and right portions (1003, 1005 and 1007) that respectively represent (a) an on-line or other business that for a fee may automatically monitor one or more water supplies, (b) one or more clients of the business, e.g., one or more municipal water companies, and (c) a regulatory authority or other entity that is to monitor or receive reporting of compliance of any one of the water supplies. FIG. 10 illustrates two hypothetical clients 1009 and 1011, each of which may be taken to be a water company, each of which may have one or more in-situ devices 1013 for monitoring a particular portion of a water delivery network (only one in-situ device is numerically labeled to simplify the illustration). In this regard, it should be assumed that the method (e.g., the business) is to automatically and/or remotely collect measurement data for the purposes of logging THM data for compliance reporting or other purposes; to this effect, the business 1003 includes a supervisory control mechanism 1015, depicted as one or more computers running software 1017 (e.g., a server system), with this system interfacing both with each client (via a client-side web interface 1019), and with a regulatory authority 1021 (via a regulatory side interface 1023). In one embodiment, the regulatory side web interface may provide a portal for regulatory authorities to remotely audit current and past individual water supply operations, with further ad-hoc tests being initiated as required, and with the business interacting with regulatory authorities on behalf of each client, if desired or appropriate, in a manner transparent to each client. Each interface 1019/1023 may permit different access levels and present different authentication requirements (e.g., a specific type or level of PKI authentication). For example, because the client side interface may be used for automated communication with each in-situ device 1013, each such device may be made to have an embedded cryptographic key for purposes of authentication; on the other hand, because regulatory interaction may involve aggregated, relatively sensitive data, two-factor or other authentication requirements may be used as a predicate for individual access by a remote human user. Regardless of the interface formats, the supervisory system can be configured to perform a number of functions, depicted at the middle of FIG. 10, thereby relieving the clients 1009 and 1011 from the need to perform these functions themselves, and minimizing the need for on-site presence or inspection by regulatory authorities. As indicated by reference numeral 1025, the method may include periodically receiving test data from each one of the plural in-situ devices 1013 via the client-side interface 1019; each instance of test data may represent an automated process that is initiated by the specific device 1013, and/or the supervisory system 1015 may also selectively initiate tests. For example, if it is determined that a specific THM concentration determined from a test is out of normal bounds, an ad hoc test may be commanded by the supervisory control system, as indicated by reference numeral 1026. The supervisory control system may perform data base management (1027), indexing each set of test data by particular provider, time and date, last known calibration, and any other desired data. As indicated by blocks 1031, 1033, 1035 and 1037, the supervisory control system (or a different electronic control system) may also test for and/or respond to maintenance events, generate alarms or take process control actions responsive to comparison of THM levels against thresholds, and generate automatic compliance reports either for the regulatory authority 1021 or a particular client 1009 or 1011. As further depicted by a dashed-line, optional block 1029, if desired, raw data may be reported to the supervisory control system 1015, with total and/or individual species THM calculations being performed by the supervisory control system 1015, on a remote basis.

As should be apparent from this description, the methods and devices provided above, by facilitating real-time, relatively same, automated THM measurement, provide for new advances not only in the measurement process, but also in terms of compliance and accountability, potentially changing the way in which water companies and regulatory authorities do business.

Various alternatives to the foregoing techniques will readily occur to those having skill in the art. To pick just a few examples, techniques mentioned above may be applied using other types of detected optical activity (e.g., other than change in visible color intensity), and halohydrocarbon extraction may be accomplished using mechanisms other than an adsorbent medium. To pick another example, the method of business described above may be applied with or without modified Fujiwara-type chemistry. Many other variations also exist. Accordingly, the foregoing discussion is intended to be illustrative only; other designs, uses, alternatives, modifications and improvements will also occur to those having skill in the art which are nonetheless within the spirit and scope of the present disclosure, which is limited and defined only by the following claims and equivalents thereto.

We claim:

1. An apparatus comprising:
    a sampling mechanism to draw water samples from a water supply;
    a measurement device to measure halohydrocarbons present in respective ones of the water samples; and
    at least one processor to intermittently control the sampling mechanism and the measurement device, so as to automate the drawing of the water samples from the water supply and the measurements of the halohydrocarbons present in the respective ones of the water samples;
    wherein the at least one processor is also to intermittently control the measurement device, so as to perform respective, calibration measurements of halohydrocarbons present in samples drawn from the water supply to which a standard, comprising a known quantity of halohydrocarbons, has been added; and
    wherein the at least one processor is to calculate halohydrocarbon concentration for each respective one of the water samples, dependent on at least one of the calibration measurements.

2. The apparatus of claim 1, wherein the at least one processor is to communicate with the sampling mechanism and the measurement device via a wide area network (WAN).

3. The apparatus of claim 1, wherein the at least one processor is to control the sampling mechanism and the measurement device to obtain the calibration measurement on a periodic basis, wherein the periodic basis is no less frequent than once per month.

4. The apparatus of claim 1, wherein:
    the apparatus further comprises
        a medium to receive the water samples and extract halohydrocarbons from the water samples, and
        a reaction vessel to receive extracted halohydrocarbons from the medium;
    the at least one processor is to cause a reagent to be added to the reaction vessel;
    the measurement device is to measure an optical property of a reaction initiated by the addition of the reagent, to measure halohydrocarbons present in respective ones of the water samples.

5. The apparatus of claim 4, wherein the reagent is a pyridine derivative characterized by a pyridine structure with one or more substitutions of hydrogen at the carbon atoms of the pyridine.

6. The apparatus of claim 1, wherein the measurement device is to measure a time-based optical property of a reaction involving halohydrocarbons from the respective ones of the water samples.

7. The apparatus of claim 6, wherein the measurement device is to obtain at least two time-differentiated measurements of the optical property, and wherein the at least one processor is to calculate concentration of a specific, predetermined specie of halohydrocarbons present in respective ones of the water samples, dependent on the at least two time-differentiated measurements of the optical property for the respective one of the water samples.

8. The apparatus of claim 6, wherein the apparatus comprises a network interface to exchange with a remote destination measurement data representing the concentration of the specific, predetermined specie of halohydrocarbons.

9. The apparatus of claim 1, wherein the standard comprises at least one of $CHCl_3$, $CHBrCl_2$, $CHBr_2Cl$ and $CHBr_3$.

10. The apparatus of claim 1, wherein the apparatus comprises a heating device to heat water samples drawn from the water supply, a source of a gas to be passed through the samples to purge out the halohydrocarbons, a trap having an adsorbent medium to isolate purged halohydrocarbons from the water samples, and fluidic transfer means to fluidically transfer extracted halohydrocarbons from the adsorbent medium to a reaction vessel.

11. The apparatus of claim 10, further comprising a mechanism to regenerate the trap, wherein the at least one processor is also to intermittently control the mechanism to regenerate the trap in between of measurement of halohydrocarbons present in respective ones of the water samples.

12. A method comprising:
    causing a sampling mechanism to draw water samples from a water supply;
    causing a measurement device to measure halohydrocarbons present in respective ones of the water samples; and
    causing at least one processor to intermittently control the sampling mechanism and the measurement device, so as to automate the drawing of the water samples from the water supply and the measurements of the halohydrocarbons present in the respective ones of the water samples;
    wherein the method further comprises causing the at least one processor to also intermittently control the measurement device so as to perform respective, calibration measurements of halohydrocarbons present in samples drawn from the water supply to which a standard, comprising a known quantity of halohydrocarbons, has been added; and
    wherein the method further comprises causing the at least one processor to calculate halohydrocarbon concentration for each respective one of the water samples, dependent on at least one of the calibration measurements.

13. The method of claim 12, wherein the method further comprises causing the at least one processor to communicate with the sampling mechanism and the measurement device via a wide area network (WAN).

14. The method of claim 12, wherein the method further comprises causing the at least one processor to control the sampling mechanism and the measurement device to obtain the calibration measurement on a periodic basis, wherein the periodic basis is no less frequent than once per month.

15. The method of claim 12, wherein the method further comprises:

receiving the water samples with a medium and extracting halohydrocarbons from the water samples, and receiving extracted halohydrocarbons from the medium into a reaction vessel;

causing a reagent to be added to the reaction vessel; and causing the measurement device to measure an optical property of a reaction initiated by the addition of the reagent, to measure halohydrocarbons present in respective ones of the water samples.

16. The method of claim 15, wherein the reagent is a pyridine derivative characterized by a pyridine structure with one or more substitutions of hydrogen at the carbon atoms of the pyridine.

17. The method of claim 12, wherein the method further comprises causing the measurement device to measure a time-based optical property of a reaction involving halohydrocarbons from the respective ones of the water samples.

18. The method of claim 17, wherein the method further comprises causing the measurement device to obtain at least two time-differentiated measurements of the optical property, and causing the at least one processor to calculate concentration of a specific, predetermined specie of halohydrocarbons present in the respective ones of the water samples, dependent on the at least two time-differentiated measurements of the optical property for the respective one of the water samples.

19. The method of claim 12, wherein the method further comprise exchanging with a remote destination via a network measurement data representing concentration of a specific, predetermined specie of halohydrocarbons, the measurement data derive from one or more of the measurements.

20. The method of claim 12, wherein the standard comprises at least one of $CHCl_3$, $CHBrCl_2$, $CHBr_2Cl$ and $CHBr_3$.

21. The method of claim 12, wherein the method further comprises causing the at least one processor to initiate a regeneration cycle following measurement of each of the water samples, so as to prepare a measurement apparatus to measure halohydrocarbons present in an ensuing one of the water samples.

22. A method comprising:

causing a sampling mechanism to draw water samples from a water supply;

causing a measurement device to measure amount of a predetermined specie of halohydrocarbons present in respective ones of the water samples, wherein the measurement device is to obtain at least two time-differentiated measurements of an optical property; and causing at least one processor to intermittently control the sampling mechanism and the measurement device, so as to automate the drawing of the water samples from the water supply and the measurements of the halohydrocarbons present in the respective ones of the water samples;

wherein the method further comprises causing the at least one processor to also intermittently control the measurement device so as to perform respective, calibration measurements of halohydrocarbons present in samples drawn from the water supply to which a standard, comprising a known quantity of halohydrocarbons, has been added;

wherein the standard comprises at least one of $CHCl_3$, $CHBrCl_2$, $CHBr_2Cl$ and $CHBr_3$; and wherein the method further comprises causing the at least one processor to calculate concentration of the predetermined specie of halohydrocarbons for each respective one of the water samples, dependent on at least one of the calibration measurements, and dependent on the at least two time-differentiated measurements of the optical property for the respective one of the water samples.

* * * * *